United States Patent [19]

Russell

[11] Patent Number: 4,784,961

[45] Date of Patent: Nov. 15, 1988

[54] FLUORESCENCE POLARIZATION METHOD FOR MONITORING FETAL LUNG MATURITY

[75] Inventor: John C. Russell, Greenfield, Wis.

[73] Assignee: Abbott Laboratories, Abbott Park, Ill.

[21] Appl. No.: 29,002

[22] Filed: Mar. 23, 1987

[51] Int. Cl.$^4$ .............................................. G01N 33/48
[52] U.S. Cl. ..................................... 436/63; 436/172; 436/907; 250/302; 250/461.2
[58] Field of Search .............. 73/60.1; 250/302, 461.2; 436/63, 71, 172, 907

[56] References Cited

U.S. PATENT DOCUMENTS

| | | |
|---|---|---|
| 4,071,770 | 1/1978 | Shinitzky et al. |
| 4,233,032 | 11/1980 | Statland et al. |
| 4,255,329 | 3/1981 | Ullman |
| 4,257,771 | 3/1981 | Yee |
| 4,351,760 | 9/1982 | Khanna et al. |
| 4,370,311 | 1/1983 | Ilekis |
| 4,388,412 | 6/1983 | Yabusaki |
| 4,420,568 | 12/1983 | Wang et al. |
| 4,476,228 | 10/1984 | Huchzermeier et al. |
| 4,476,229 | 10/1984 | Fino et al. |
| 4,481,136 | 11/1984 | Khanna et al. |
| 4,492,762 | 1/1985 | Wang et al. |
| 4,510,251 | 4/1985 | Kirkemo et al. |
| 4,585,862 | 4/1986 | Wang et al. |
| 4,588,697 | 5/1986 | Khanna et al. |
| 4,593,089 | 6/1986 | Wang et al. |
| 4,681,859 | 7/1987 | Kramer |

FOREIGN PATENT DOCUMENTS

0010917 5/1980 European Pat. Off.
2111476A 7/1983 United Kingdom.

OTHER PUBLICATIONS

Tait et al. "Improved Fluorescence Polarization Assay For Use In Evaluating Fetal Lung Maturity, I, Development of the Assay Procedure" (Clinical Chemistry) (1986), vol. 32, No. 2.
Foerder et al. "Improved Fluorescence Polarization Assay For Use In Evaluating Fetal Lung Maturity, II, Analytical Evaluation and Comparison with the Lecithin/Sphingomyelin Ratio" Clinical Chemistry, vol. 32, No. 2 (1986).
A. Jobe, et al., *Journal of Applied Physiology*, 58(4):1246–1251 (1985).
Jobe et al.; Lung Protein Leaks in Ventilated Lambs: Effect of Gestational Age; CA102(23):201978y 1985.
Ashwood et al. "Improved Fluorescence Polarization Assay For Use in Evaluating Fetal Lung Maturity, III, Retrospective Clinical Evaluation and Comparison with the Lecithin/Sphigomylin Ration" (Clinical Chemistry) (1986), vol. 32, No. 2.
Peterson et al. "The Effect of Fetal Pulmonary Surfactant Production on the Apparant Microviscosity of Amniotic Fluid Measured by Fluoresence Polarization" (Scand. J. Clin. Lab. Invest.) No. 43, pp. 41–47 (1983).
Lee, et al., Chemical Abstracts, 88(3):529, col. 1, abstract-No. 21 578b (Jan. 16, 1978).
Herberer, et al., Chemical Abstracts, 104(17):689, col. 1, abstract-No. 148 802z (Apr. 28, 1986).
Nichols, et al., Chemical Abstracts, 96(17):352, col. 1, abstract-No. 138 374p (Apr. 26, 1982).
Barkai, et al., *Obstetrics and Gynecology*, 1985 Apr. 65(4) 573–9 (Medline abstract enclosed).
Shipchandler, et al., *Analytical Biochemistry*, 162:89–101 (1987).
*Geigg Scientific Tables*, vol. 1, 8th Edition, Editor C. Lentner, pp. 197–212 (1981).

*Primary Examiner*—Michael S. Marcus
*Assistant Examiner*—Timothy M. McMahon
*Attorney, Agent, or Firm*—Robert W. Stevenson; Martin L. Katz

[57] ABSTRACT

The present invention is directed to a fluorescence polarization method for monitoring fetal lung maturity, to various components needed for preparing and carrying out such monitoring, and to methods of making these components.

3 Claims, 3 Drawing Sheets

FLUORESCENCE POLARIZATION METHOD FOR MONITORING FETAL LUNG MATURITY

CROSS REFERENCE TO RELATED APPLICATIONS

This application is a continuation in part of co-pending application Ser. No. 886,472, filed July 15, 1986.

BACKGROUND OF THE INVENTION

1. Technical Field

The present invention relates to a method and reagents for a fluorescence polarization assay procedure for determining fetal lung maturity from a sample of amniotic fluid, and to a method for preparing the reagents.

2. Background Art

Since the discovery in the early 1970's that fetal lung maturity can be assessed from amniotic fluid collected via amniocentesis, the management of preterm deliveries has greatly improved. A variety of methods have been developed to measure some feature of amniotic fluid surfactant, each of which possesses both advantages and disadvantages. The methods currently used relate fetal lung maturity to the composition of the surfactant secreted by the fetal lungs. The most widely used test measures the lecithin/sphingomyelin (L/S) ratio of the phospholipids in the fetal lung surfactant. An L/S ratio greater than 2.0 is generally taken to indicate fetal lung maturity. This test is tedious, reguiring 2 to 4 hours to perform, and the large number of individual variations in technique results in poor reproducibility between laboratories.

The foam stability index (FSI) test is another method used to assess fetal lung maturity. A sample of amniotic fluid is shaken, forming a layer of foam at its surface which is stable for several minutes. In the presence of 40-50% ethanol, the foam layer disappears rapidly. The maximum concentration of ethanol at which the foam remains is called the foam stability index. An index of greater than 0.47 is generally taken to indicate fetal lung maturity. This method has the disadvantage of requiring a large volume of amniotic fluid. In addition, the subtle difference between a "stable" and "unstable" foam layer creates difficulties in reading a result.

The use of fluorescence polarization for monitoring fetal lung maturity was first described by Shinitzky et al. in 1976 [Br J Obstet Gynaecol (1976), 83, 838]. The technique involves mixing the dye diphenyl hexatriene (DPH) with a sample of amniotic fluid. The dye associates with the liposomes formed by the surfactants present in the amniotic fluid. The sphingomyelin present in amniotic fluid from immature fetuses forms liposomes having high microviscosity. In this environment the motion of the dye is restricted and, upon excitation with plane polarized light, a high degree of polarization is retained in the fluorescence. In the amniotic fluid from mature fetuses the surfactant liposomes contain a high level of lecithin which decreases the microviscosity. This allows the dye to have greater freedom of motion, and the fluorescence polarization is thereby decreased. A fluorescence polarization of less than 0.310 is taken to indicate fetal lung maturity. While Shinitzky's method was shown to be predictive of lung maturity, it has several disadvantages: (1) the results show a poor correlation with the more widely accepted L/S ratio; (2) the required instrumentation is expensive and frequently unavailable in hospitals; and (3) the stock solutions of reagents for the test are highly unstable and must be prepared daily.

Recent studies by Tait et al. [Clin Chem (1986) 32/2 248-254], Foerdor et al. [Clin Chem (1986) 32/2 255-259] and Ashwood et al. [Clin Chem (1986) 32/2 260-264] have made use of the Abbott TDx[R] fluorescence polarization analyzer to measure the fluorescence polarization in amniotic fluid of the dye 1-palmitoyl-2,6-[(7-nitro-2,1,3-benzoxadiazol-4-yl) amino]caproyl phosphatidyl choline (NBD-PC):

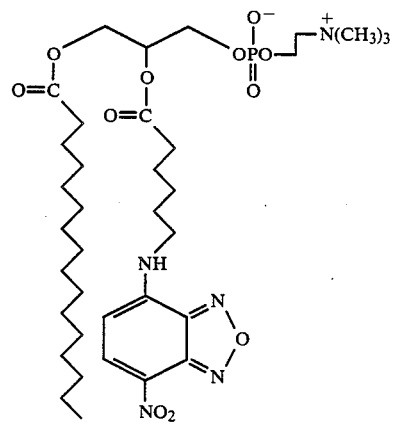

NBD-PC is a synthetic derivative of lecithin having solubility and binding characteristics very similar to those of lung surfactant. When added to amniotic fluid, the dye should become part of the liposomes of lung surfactant, with the fluorophore associated with the hydrophobic region of the aggregate. Just as with DPH, the microviscosity of the environment of the dye in the liposome should affect its fluorescence polarization. The fluorescence polarization was seen to be high in immature samples and to decrease with increasing maturity, as with the DPH system. Good correlation was seen with both the L/S ratio and with the clinical outcome of the pregnancy.

The present invention involves the use of N-[-N-palmitoyl- -N-(4-nitrobenz-2-oxa 1,3 diazole)-L-lysine]-2-aminoethanol,N(trimethylaminoethanol) phosphate (PC16), a fluorescent probe similar in activity to NBD-PC but with its structure modified so as to enhance its long term chemical stability:

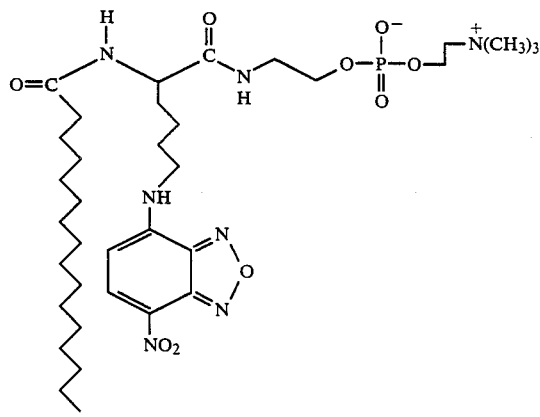

The dye has been tested in amniotic fluid and in a variety of solutions developed to simulate features of amniotic fluid. Results presented herein clearly show the mechanism of its activity to involve association of the dye with the protein albumin as well as with surfactant. The fluorescence polarization or fluorescence intensity results can be calibrated and translated to a surfactant-/albumin ratio, which can be reported as a highly repeatable index to fetal lung maturity.

SUMMARY OF THE INVENTION

The present invention is directed to a fluorescence polarization method for monitoring fetal lung maturity, to various components needed for preparing and carrying out such monitoring, and to methods of making these components.

A first aspect of the invention relates to the discovery of unique fluorescent probes characterized by novel structures and excellent chemical stability. These fluorescent probes can be represented by the structural formula:

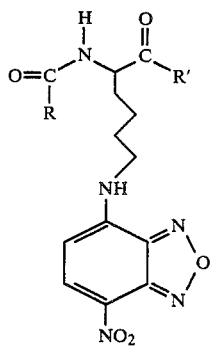

wherein:

R is a saturated or unsaturated branched or straight alkyl chain having from 5 to 23 carbon atoms; and R' is a hydrophilic amine-containing group, which may be anionic, cationic, zwitterionic or neutral.

In a preferred embodiment of this aspect of the invention, R is a saturated straight alkyl chain having from 13 to 17 carbon atoms, and the polar amine-containing group is zwitterionic.

According to a second aspect of the invention, the aforementioned fluorescent probes are prepared by amidating a fluorescent derivative of lysine.

A third aspect of the invention relates to a method of determining fetal lung maturity by measuring the ratio of surfactant to albumin in a sample of amniotic fluid.

A fourth aspect of the invention relates to calibrators for use in a determination of fetal lung maturity. The calibrators comprise the combination of: (1) serum albumin; and (2) one or more surfactants in an aqueous buffer. In one preferred embodiment of this aspect of the invention, the surfactant is a nonionic surfactant; in a second preferred embodiment, a combination of anionic and nonionic surfactants is employed. In the latter preferred embodiment, the nonionic surfactant is Triton X-100® and the anionic surfactant is decanesulfonic acid.

DETAILED DESCRIPTION OF THE INVENTION

Figure 1:
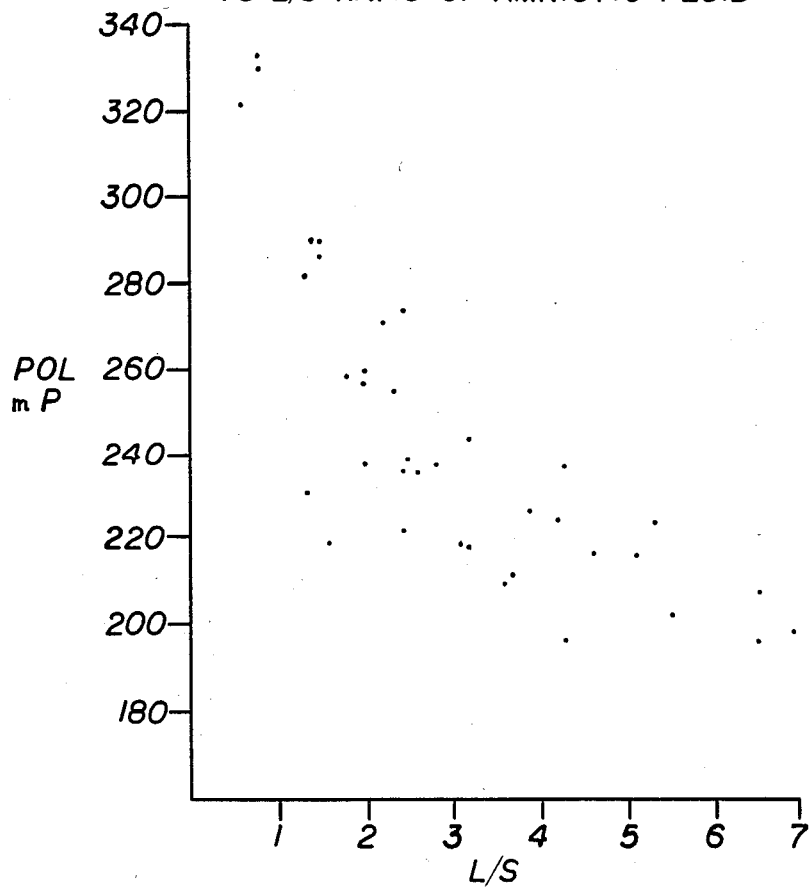
FIG. 1 is a graph of Fluorescence Polarization vs L/S Ratio of Amniotic Fluid.

FIG. 1 shows the fluorescence polarization of PC16 in amniotic fluid samples plotted versus the L/S ratio of these samples. At low L/S ratios the fluorescence polarization is high, with a maximum of about 330 mP. As the L/S ratio increases, the fluorescence polarization decreases to about 200 mP at high L/S ratios.

Attempts were made by Applicant to duplicate the fluorescence polarization values obtained with amniotic fluid samples by using dispersions of lecithin and sphingomyelin in buffer.

TABLE 1

| Fluorescence polarization of PC16 in dispersions of lecithin (lec) and sphingomyelin (sph). | | |
|---|---|---|
| lec mg/l | sph mg/l | polarization mP |
| 0 | 20 | 172 |
| 20 | 20 | 132 |
| 40 | 20 | 132 |
| 80 | 20 | 137 |
| 80 | 0 | 120 |

Figure 2:
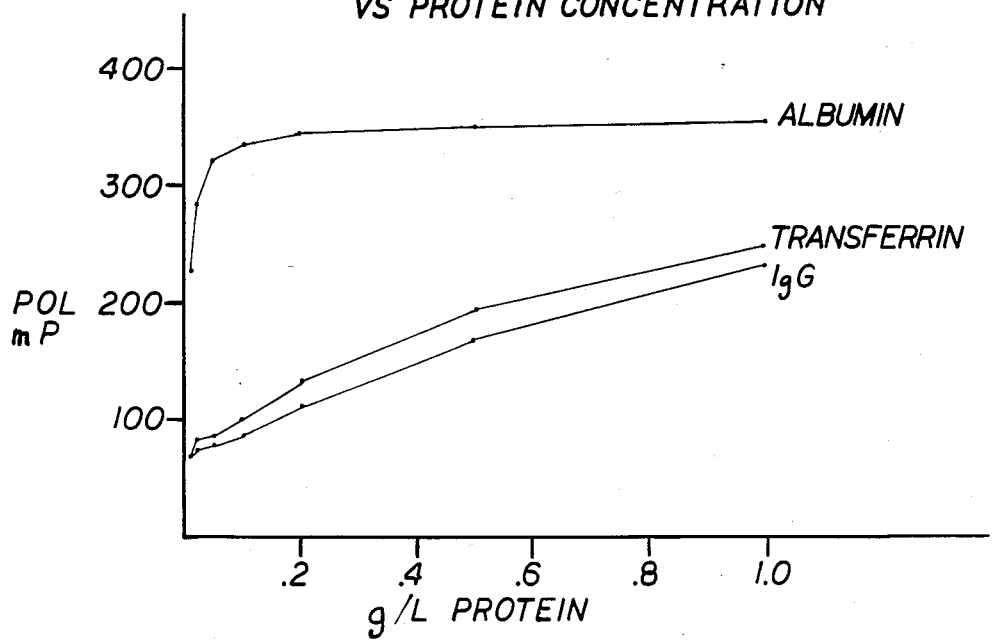
FIG. 2 is a graph of Fluorescence Polarization vs Protein Concentration.

As Table 1 indicates, consistently low fluorescence polarization values were obtained regardless of the L/S ratio. To achieve a high polarization at low surfactant levels, some other component of amniotic fluid was thought to be binding PC16. Because proteins are present in amniotic fluid in greater concentrations than surfactants, several of the proteins most prevalent (albumin, transferrin, IgG) were tested to assess their binding to PC16. Results are presented in FIG. 2.

Albumin, which shows by far the strongest effect on polarization, is also that protein present in amniotic fluid at the highest concentration, accounting for 60–70% of total protein.

The addition of phospholipid dispersions to albumin solutions in concentrations similar to those seen in amniotic fluid strongly decreases the observed fluorescence polarization.

Figure 3:
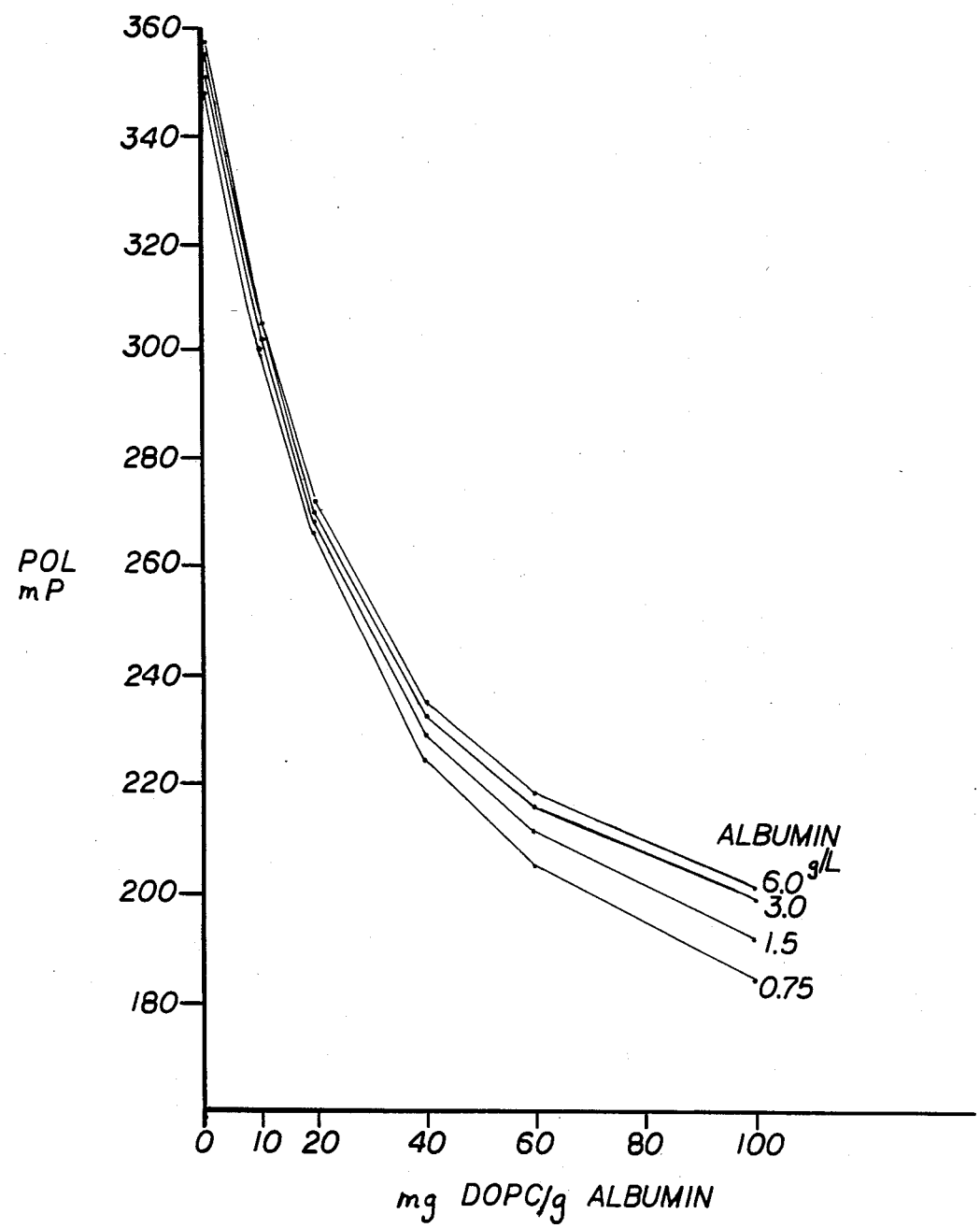
FIG. 3 is a graph of Fluorescence Polarization vs Surfactant/Albumin Ratio Effect of Changing Surfactant Composition.

In a system of constant surfactant composition and dispersion, a curve can be drawn in which the measured polarization is dependent on the relative amounts of surfactant and albumin. A high surfactant/albumin ratio results in a low polarization and a low ratio gives a high polarization. This is shown in FIG. 3.

In amniotic fluid the albumin concentration shows considerable variation. At gestational ages between 30 and 40 weeks the mean concentration has been reported to be 2 g/l with a standard deviation of 1 g/l. The albumin concentrations of the amniotic fluid samples of FIG. 1 have a mean of 1.6 g/l and a range from 0.86 to 3.16 g/l. The effect of the albumin concentration on the curve is shown in FIG. 3. For each surfactant/albumin ratio on the X axis, a concentrated dioleyl phosphatidyl choline (DOPC)/albumin solution was diluted with buffer to several concentrations spanning the range of albumin concentrations found in amniotic fluid. It is apparent that at a constant surfactant/albumin ratio, increasing the albumin concentration results in a somewhat higher polarization, and that this effect is most pronounced at high surfactant/albumin ratios. At 80 mg DOPC/g albumin the ratio predicted from the 1.5 g/l albumin curve differs from the actual level by as much as 16% at 3 g/l. However, at low and intermediate surfactant/albumin ratios, much less variation is seen. At 30 mg DOPC/g albumin, for example, only a 6% difference is seen.

Figure 4:
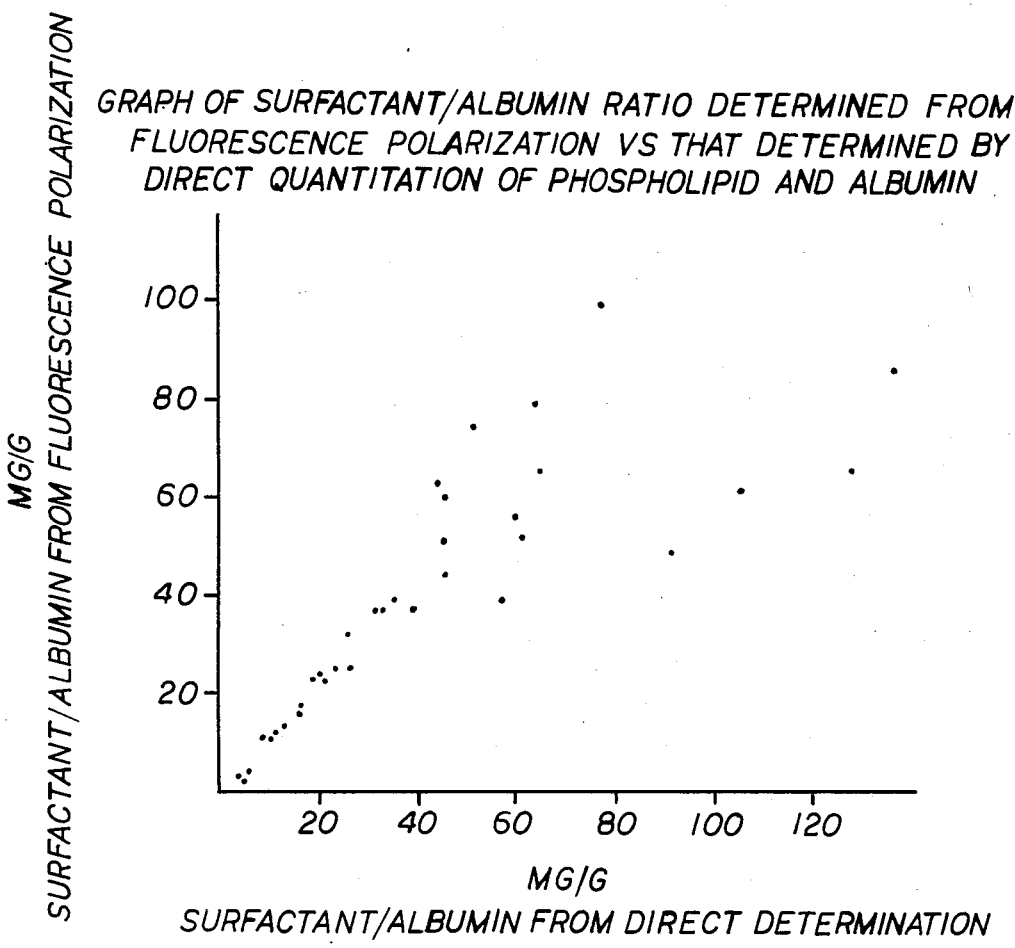
FIG. 4 is a graph of Surfactant/Albumin Ratio Determined From Fluorescence Polarization vs That Determined by Direct Quantitation of Phospholipid and Albumin.

To assess the accuracy of this system in measuring surfactant/albumin ratios for amniotic fluid, the samples were subjected to an independent measurement. The total phospholipid phosphorus was determined by digestion of the extracted phospholipid, and measurement of the resultant phosphate, then converted to mg/l surfactant based on the molecular weight of DOPC (786.1) and divided by the albumin concentration to give mg surfactant/g albumin. The surfactant/albumin ratio found by this method was compared with that found from fluorescence polarization data. Results are shown in Table 2 and FIG. 4. Table 2 also contains data as to surfactant/albumin ratios found from fluorescence intensity measurement.

TABLE 2

Measurements made on amniotic fluid samples taken for fetal lung maturity testing.

| L/S | POL mP | CALIBRATED[a] MG/G | ALBUMIN G/L | PHOSPHO LIPID MG/L | DIRECT[b] MG/G | RELATIVE INTENISTY |
|---|---|---|---|---|---|---|
| 0.6 | 322.44 | 4.15 | 3.16 | 16.9 | 5.4 | 112 |
| 0.8 | 332.70 | 2.66 | 2.82 | 12.5 | 4.4 | 100 |
| 0.8 | 329.76 | 3.06 | 2.65 | 10.0 | 3.8 | 100 |
| 1.3 | 282.49 | 13.26 | 1.52 | 19.3 | 12.7 | 141 |
| 1.3 | 231.23 | 44.13 | 1.34 | 61.9 | 46.1 | 256 |
| 1.4 | 289.90 | 11.05 | 1.60 | 13.5 | 8.4 | 131 |
| 1.5 | 290.32 | 10.93 | 2.32 | 23.6 | 10.2 | 127 |
| 1.5 | 286.61 | 11.99 | 1.06 | 11.4 | 10.8 | 120 |
| 1.6 | 219.49 | 59.99 | 1.39 | 64.4 | 46.2 | 230 |
| 1.8 | 258.85 | 22.99 | 1.66 | 31.2 | 18.8 | 148 |
| 2.0 | 238.01 | 37.38 | 1.29 | 51.1 | 39.6 | 213 |
| 2.0 | 259.79 | 22.50 | 1.89 | 40.6 | 21.4 | 179 |
| 2.0 | 256.95 | 24.02 | 1.72 | 33.7 | 19.7 | 175 |
| 2.2 | 272.08 | 16.96 | 1.76 | 29.1 | 16.5 | 144 |
| 2.3 | 255.25 | 24.98 | 1.39 | 32.9 | 23.7 | 173 |
| 2.3 | 255.40 | 24.89 | 1.71 | 44.6 | 26.0 | 184 |
| 2.4 | 236.05 | 39.19 | 1.75 | 100.6 | 57.5 | 232 |
| 2.4 | 221.65 | 56.56 | 1.62 | 97.8 | 60.3 | 186 |
| 2.4 | 273.76 | 16.31 | 1.20 | 19.4 | 16.2 | 142 |
| 2.5 | 238.70 | 36.76 | 1.53 | 50.6 | 33.1 | 199 |
| 2.6 | 235.86 | 39.37 | 1.45 | 51.7 | 35.5 | 212 |
| 2.8 | 238.12 | 37.28 | 1.07 | 34.5 | 32.3 | 210 |
| 3.1 | 218.78 | 61.17 | 1.73 | 183.9 | 106.3 | 283 |
| 3.2 | 244.32 | 32.18 | 1.07 | 28.1 | 26.1 | 197 |
| 3.2 | 217.65 | 63.13 | 1.59 | 71.7 | 45.2 | 229 |
| 3.6 | 209.85 | 79.36 | 1.20 | 77.9 | 64.7 | 266 |
| 3.7 | 211.94 | 74.47 | 0.99 | 51.8 | 52.5 | 223 |
| 3.9 | 227.06 | 49.05 | 1.19 | 109.0 | 91.9 | 186 |
| 4.2 | 224.70 | 52.16 | 1.67 | 103.8 | 62.3 | 297 |
| 4.3 | 196.90 | >100 | 1.10 | 113.9 | 103.9 | 277 |
| 4.3 | 238.32 | 37.10 | 1.56 | 50.7 | 32.4 | 193 |
| 4.6 | 216.77 | 64.72 | 1.77 | 117.3 | 66.3 | 291 |
| 5.1 | 216.96 | 64.36 | 1.36 | 176.1 | 129.1 | 280 |
| 5.3 | 225.27 | 51.39 | 1.50 | 68.9 | 45.9 | 241 |
| 5.5 | 203.08 | 98.79 | 1.00 | 78.5 | 78.5 | 278 |
| 6.5 | 207.87 | 84.41 | 1.54 | 212.4 | 137.7 | 329 |
| 6.5 | 197.10 | >100 | 0.97 | 84.0 | 86.3 | 297 |
| 6.9 | 198.83 | >100 | 0.86 | 113.4 | 131.7 | 296 |

There is good agreement between the two methods out to about 40 mg/g, above which level the scatter in results increases considerably. While most samples in this region continue to show agreement within that expected from the results of FIG. 4, some show significantly lower values by fluorescence polarization than by direct measurement. This tendency probably results from changes in the composition of the surfactant at high levels of maturity. Since this effect occurs only in samples assessed as highly mature by all methods, the inaccuracies it produces are clinically insignificant. In the region of surfactant/albumin ratios below about 40 mg/g, which covers the immature and borderline region, excellent agreement between the two methods is seen. As can be seen from Table 2, the flourescence intensity shows about a three fold increase from low to high L/S ratio, however, this effect is not so strong as the fluorescence polarization effect.

The good correlation of fluorescence polarization of PC16 with L/S ratio indicates that this system is useful for assessment of fetal lung maturity. The use of the amniotic fluid surfactant/albumin ratio as an index of fetal lung maturity requires the acceptance of albumin as a reference substance, like sphingomyelin in the L/S ratio. While the rate of production of albumin may not be the same for all pregnancies, it can be assumed that the rate of elimination, by fetal swallowing, is the same as that for the surfactant. In the range of 0.8-3 g/l albumin, which includes the vast majority of amniotic fluid samples, fluorescence polarization provides an accurate measure of the surfactant/albumin ratio in the region in which accuracy is most important. A simple test for albumin concentration, such as that presented in the experimental section, would provide for a measure of the absolute surfactant concentration, if this is desired. This test appears to provide a precise index for fetal lung maturity which should be reproducible betwen laboratories.

For the aforedescribed experiments, human albumin, IgG, transferrin, and all the phospholipids used were obtained from Sigma Chemical Co., St. Louis, Mo. Stock solutions were prepared in 0.1M phosphate buffer (pH 7.0), by weight, with the exception of albumin, the concentration of which was adjusted to the desired value. Phospholipid solutions were prepared in methanol. Typically, 1.00 ml methanolic solution containing 10.0 mg phospholipid was added, and the mixture sonicated with the intermediate tip of a Virsonic Cell Disruptor with intensity set at the maximum for the tip. Sonication time was 8 minutes, during which the solution became clear and the temperature rose from 24° to 76°.

The present invention involves the use of derivatives of 4-nitrobenz-2-oxa-1,3-diazole (NBD). A necessary property of NBD and its derivatives for usefulness as tracer compounds herein is the fluorescence of NBD. NBD and its derivatives have the following general structure:

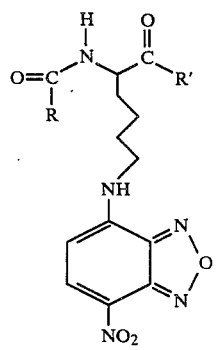

The tracers described in the invention all have a surfactant structure, i.e., they contain hydrophobic and hydrophilic portions on the same molecule. As surfactants they have a tendency to bind to interfacial regions when dissolved in aqueous solutions. In amniotic fluid, proteins (primarily from maternal serum) and phospholipid aggregates (primarily from fetal lung) provide the interfacial regions to which the tracers bind. Albumin shows a much greater tendency to bind these tracers than the other proteins found in amniotic fluid, and since it is the protein in greatest concentration, the approximation that albumin is the only binding protein is valid. In aqueous solutions containing only albumin the tracer PC16 shows a fluorescence polarization of about 360 mP. In solutions containing only a dispersion of the type of phospholipids secreted by the fetal lung into amniotic fluid, the tracer shows a fluorescence polarization of about 140 mP. In mixtures containing both albumin and surfactant, and in real amniotic fluid, the tracer shows intermediate polarizations; the exact polarization is dependent on the ratio of surfactant to albumin.

The tracers of the present invention have the general structure shown above, wherein R represents a saturated or unsaturated branched or straight alkyl chain having from 5 to 23 carbon atoms, and R' represents a hydrophilic amine-containing group which may be anionic, cationic, zwitterionic or neutral.

Specific examples of R' include the following:

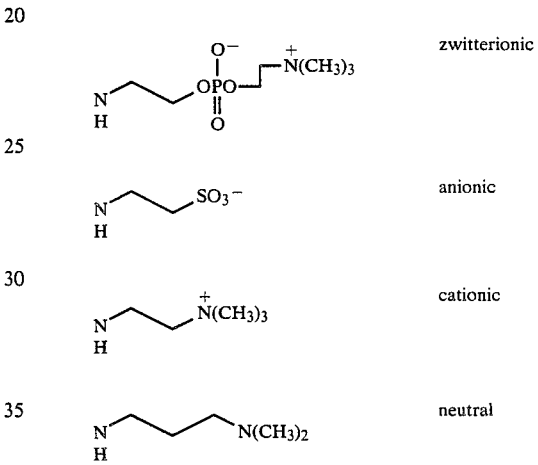

The tracers are derivatives of lysine which has been linked at the 4-position of NBD through the epsilon nitrogen of lysine. The alpha nitrogen of the lysine derivative is acylated with a saturated or unsaturated fatty acid having from 5 to 23 carbon atoms. The hydrophilic group R' is added via reaction with the carboxyl group of the lysine with an amino nitrogen of the hydrophilic group.

As shown in the following reaction scheme, the tracers may be prepared by using epsilon amino and carboxyl protected lysine as the starting material (1). The doubly protected lysine is acylated with the desired fatty acid and the two protecting groups are removed. The resulting compound (2) is reacted with 4-chloro-7-nitrobenz-2-oxa-1,3-diazole to give the key intermediate (3). The hydrophilic group is then added by amidation of the carboxyl group to give the probe (4).

An alternate route to key intermediate (3) starts with alpha-amino protected lysine (5). This is reacted with 4-chloro-7-nitrobenz-2-oxa-1,3-diazole to give (6). After deprotection and acylation, the key intermediate (3) is obtained.

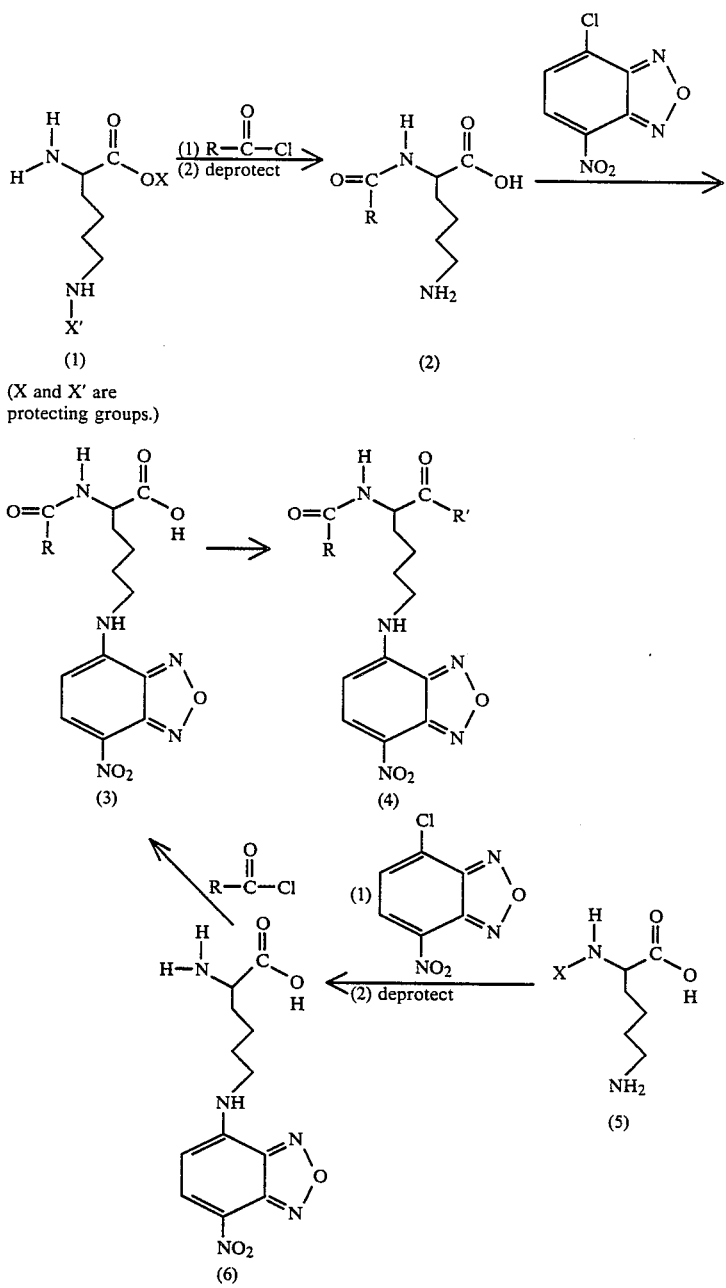

(X and X' are protecting groups.)

The fluorescence polarization of the tracer is determined by the ratio of surfactant to albumin in the sample. Consequently, calibrators for the assay should consist of a solution of surfactant and albumin. Unfortunately, phospholipids of the type found in lung surfactant are chemically unstable in solution, and deteriorate substantially over a period of days. Stable calibrator solutions can be prepared from a mixture of albumin and any of a variety of chemically stable surfactants. The surfactants may be anionic or nonionic, or a mixture of the two. In the preferred system, six calibrators are used. The calibrator corresponding to a surfactant/albumin ratio of zero, or 0 mg/g, consists of 2 g/l human serum albumin in 0.1M sodium phosphate buffer, pH 7.0, with 0.1% sodium azide added as a preservative. The remaining calibrators use the same buffer except that bovine serum albumin is substituted for human albumin, and the solutions contain 0.04% Triton X-100® (a nonionic surfactant) and decanesulfonic acid sodium salt, the concentration of the latter being adjusted so that the fluorescence polarization of the solution matches that of a freshly prepared solution containing the desired ratio of phospholipid to albumin. Table 3 lists the desired ratios and corresponding decanesulfonic acid concentrations.

TABLE 3

| Calibrator | mg Surfactant/g Albumin | Decanesulfonic acid (M) |
|---|---|---|
| B | 10 | $1.7 \times 10^{-4}$ |
| C | 20 | $3.8 \times 10^{-4}$ |
| D | 40 | $7.8 \times 10^{-4}$ |
| E | 60 | $12.2 \times 10^{-4}$ |
| F | 100 | $22.4 \times 10^{-4}$ |

Other suitable anionic surfactants include sodium dodecyl sulfate and its homologs from $C_8$ to $C_{16}$. Other suitable nonionic surfactants include polyoxyethylene 10-laurel ether and its alkyl homologs from $C_{12}$ to $C_{18}$ and polyoxyethylene homologs from 4 to 23.

The preferred assay procedure is especially designed to be used in conjunction with the Abbott TDx ® polarization analyzer available from Abbott Laboratories, Irving, Tex. Software was developed to utilize the automated pipetting and measurement capabilities of the TDx ® instrument. A 300 ul sample of amniotic fluid or calibrator or control and 600 ul of TDx ® dilution buffer are pipetted into the cuvette and incubated 7 minutes, after which the horizontal and vertical components of the fluorescence are measured. Concentrated fluorescent probe (25 ul), sample (150 ul) and dilution buffer (275 ul) are added, and the mixture is incubated 15 minutes, after which the fluorescence is again measured, the background subtracted, and the net polarization and intensity determined. The final concentration of PC16 is $1.2 \times 10^{-6}$M in 1.35 ml solution.

Amniotic fluid collected from transabdominal amniocentesis is filtered through a glass fiber filter (supplied). 0.5 ml is placed in the sample well of the TDx ® Unit Dose FLM cartridge in a TDx ® carousel. The carousel is placed in the TDx ® analyzer and the "RUN" button is pushed. After 30 minutes, the result is printed out.

The fluorescence polarization value of each calibrator, control or sample is determined and is printed on the output tape of an instrument such as the Abbott TDx ® polarization analyzer. A standard curve is generated in the instrument by plotting the polarization of each calibrator versus its nominal concentration using nonlinear regression analysis. The concentration of each control or sample is read off the stored calibration curve and printed on the output tape.

If a manual assay is being performed, the sample is mixed with dilution buffer and a background reading is taken. The tracer is mixed with the solution and, after incubation, the polarization reading is taken.

It should be understood that the foregoing detailed description and the following examples are intended to be illustrative, but not limiting, with respect to the scope of the present invention. Various modifications will become apparent to one skilled in the art, and thus it is intended that the scope of the invention be defined solely by the claims and legal equivalents thereof.

EXAMPLES

Examples I through XV describe experiments that were performed in accordance with the concepts of the present invention.

EXAMPLE I

This example illustrates the preparation of N-palmitoyl-N- -t-BOC-L-lysine-t-butyl ester.

N- -t-BOC-L- lysine-t-butyl ester hydrochloride (1.065 g) was dissolved in 7.0 ml dry pyridine. Palmitoyl chloride (1.0 g) was added over 2 minutes. The mixture was stirred at 40° for 1 hour. The solvent was then removed, leaving a reddish brown residue. This was dissolved in 50 ml methylene chloride and extracted with 3 volumes of 50 ml 0.1N sodium hydroxide. The organic fraction was dried with anhydrous sodium carbonate and the solvent removed, yielding 2.03 g yellow oil.

EXAMPLE II

This example illustrates the preparation of N- -palmitoyl lysine.

N- -palmitoyl-N- -t BOC-L- lysine-t-butyl ester (2.03 g) was dissolved in 7.0 ml methylene chloride. 4.0 ml trifluoroacetic acid was added and the mixture stirred for 16 hours. The solvent was removed by evaporation. The resulting orange oil was dissolved in 8 ml methanol. The solution was neutralized to pH paper by adding 30% ammonium hydroxide. The resulting solid was separated from the solvent by centrifugation and decanting the solvent. After drying, 830 mg off-white powder was collected.

EXAMPLE III

This example illustrates the preparation of N- -palmitoyl-N- -(N-4-nitrobenzo-2-oxa-1,3-diazole)lysine.

N- -palmitoyllysine (769 mg) and 7-chloro-4-nitrobenz-2-oxa-1,3-diazole(500 mg) were placed in 15 ml methanol. 348 ul triethylamine was added and the mixture heated to reflux under a positive pressure of nitrogen. The mixture was stirred 2½ hours at 35°-40°, after which the solvent was removed and the residue passed through a column of silica gel with a solvent consisting of chloroform:methanol:acetic acid (100:5:2). The fractions containing the desired product were collected and the solvent was removed. Crystallization from methanol/water at −20° yielded 535 mg red powder.

EXAMPLE IV

This example illustrates the preparation of N-[-N-palmitoyl- -N-(4-nitrobenz-2-oxa-1,3-diazole)-L-lysine[-2-aminoethanol,N aminoethanol phosphate.

N- -palmitoyl-N -(N-4-nitrobenzo-2-oxa-1,3-diazole-)lysine (230 mg) was dissolved in 1.0 ml dimethylsulfoxide along with 158 mg dicyclohexyl carbodiimide, 90 mg 1-hydroxybenzotriazole and 100 ul pyridine. After 10 minutes of stirring, this solution was added in 100 ul aliquots over 30 minutes to a solution of diethanolamine phosphate perchlorate (209 mg), pyridine (100 ul) , and triethylamine (100 ul) in 1.5 ml dimethyl sulfoxide. After 60 minutes of stirring, the mixture was streaked onto preparative thin-layer chromatography plates and allowed to dry overnight in a vacuum oven at 25°. The plates were developed with chloroform:methanol:30% ammonium hydroxide (60:40:2). The desired product was eluted from the silica with methanol.

EXAMPLE V

This example illustrates the preparation of N-[-N-palmitoyl- -N-(4-nitrobenz-2-oxa-1,3-diazole)-L-lysine[-2-aminoethanol,N(trimethylaminoethanol) phosphate.

N-[-N-palmitoyl- -N-(4-nitrobenz-2-oxa-1,3-diazole)-L-lysine]-2-aminoethanol,N-aminoethanol phosphate (prepared in Example IV, supra) dissolved in 20 ml methanol was mixed with 50 mg sodium carbonate and 0.5 ml methyl iodide and stirred 2 hours. The solvent was decanted from the white solid, reduced to 3 ml by evaporation and streaked onto reverse phase preparative thin layer chromatography plates. The plates were developed with methanol:chloroform:water:ammonium hydroxide (80:20:20:2) to give the probe.

EXAMPLE VI

This example illustrates the preparation of N- -myristoyl-N- -t-BOC-L-lysine-t-butyl ester.

N- -t-BOC-L-lysine-t-butyl ester (320 mg) was dissolved in pyridine (3 ml). Myristoyl chloride (360 mg)

was added dropwise with stirring. When addition was complete, the pyridine was removed by evaporation and the residue extracted between ethyl ether and 0.1M sodium hydroxide. The solvent was evaporated from the organic layer leaving an oily residue which became a waxy solid upon cooling.

EXAMPLE VII

This example illustrates the preparation of N- -myristoyl lysine.

The waxy solid prepared in Example VI, supra, was dissolved in 6 ml of trifluoroacetic acid:methylene chloride (1:1). After 4 hours the solvent was evaporated off, leaving a clear viscous oil. This was dissolved in ethanol and 30% ammonium hydroxide added dropwise. When the solution was neutral to pH paper, a white precipate began to form. Centrifugation and drying yielded 250 mg of white crystals.

EXAMPLE VIII

This example illustrates the preparation of N- -4-nitrobenzo-2-oxa-1,3-diazole)-N- -myristoyl lysine.

101 mg of N- myristoyl lysine, 66 mg 7-chloro-4-nitrobenz-2-oxa-1,3-diazole, and 82 mg of diisopropylethylamine were dissolved in 5 ml methanol and stirred for 6 hours. The solvent was removed and the residue passed through silica gel, eluting with chloroform:methanol:acetic acid (95:5:1). Removal of solvent left 118 mg of reddish brown oil.

EXAMPLE IX

This example illustrates preparation of an anionic derivative of the fluorescent probe.

N- -(N-4-nitrobenzo-2-oxa-1,3-diazole)-N-myristoyl lysine (20 mg), dicyclohexyl carbodiimide (20 mg), hydroxybenzotriazole (8 mg) and taurine (20 mg) were mixed with 0.4 ml pyridine and heated to about 70° for 15 minutes. Preparative thin-layer chromatography on silica plates using chloroform:methanol (4:1) yielded the pure probe.

EXAMPLE X

This example illustrates preparation of N- -11-eicosenoyl lysine.

N- -t-BOC-L-lysine-t-butyl ester (514 mg) was dissolved in 3 ml of pyridine. 11-eicosenoyl chloride (500 mg) was added dropwise with stirring. The solvent was removed by evaporation and the residue extracted between methylene chloride (5 ml) and water (5 ml). The organic layer was removed from the water layer and mixed with 5 ml trifluoroacetic acid. After 4 hours the solvent was removed, yielding a light brown liquid.

EXAMPLE XI

This example illustrates the preparation of N- -(N-4-nitrobenzo-2-oxa-1,3-diazole)-N- -11-eicosenoyl lysine.

N- -11-eicosenoyl lysine (one-half the product of the reaction in Example X, supra) was dissolved in 5 ml methanol. Methanolic potassium hydroxide was added until the mixture was neutral to pH paper. 7-chloro-4-nitrobenz-2-oxa-1,3-diazole (150 mg) and triethylamine (101 mg) were added. The mixture was stirred for 16 hours. Chromatography on silica-gel using chloroform:methanol:acetic acid (95:5:1) yielded 130 mg of reddish brown oil.

EXAMPLE XII

This example illustrates the preparation of a cationic derivative of the probe N- -(N-4-nitrobenzo-2-oxa-1,3-diazole)- -11-eicosenoyl lysine.

The method of Example IX, supra, was employed, with the exception that N,N,N-trimethylaminoethylenediamine hydrochloride was substituted for taurine.

EXAMPLE XIII

This and subsequent examples illustrate an alternative route for preparation of the intermediate N- -palmitoyl-N- -(N-4-nitrobenzo-2-oxa1,3-diazole)lysine. This example illustrates the preparation of N- -t-BOC-N- -(N-4-nitrobenzo-2-oxa-1,3-diazole)lysine.

N- -t-BOC-L-lysine (9.0 g) was dissolved in 250 ml of 1N sodium bicarbonate. 4-chloro-7-nitrobenzo-2-oxa-1,3-diazole (7.29 g) was dissolved in 225 ml methanol and added dropwise over 30 minutes. After 16 hours of stirring under a nitrogen atmosphere in the dark, the solution was adjusted to pH 3 by addition of 6N hydrochloric acid. The aqueous solution was extracted with methylene chloride. The methylene chloride layers were combined, dried with anhydrous magnesium sulfate and evaporated, leaving 7.29 g of a dark red oil.

EXAMPLE XIV

This example illustrates the preparation of N- -(N-4-nitrobenzo-2-oxa-1,3-diazole) lysine.

N- -t-BOC-N- -(N-4-nitrobenzo-2-oxa-1,3-diazole) lysine (7.29 g) was dissolved in 150 ml methylene chloride. 30 ml trifluoroacetic acid was added, and the mixture stirred 10 minutes at room temperature. The solvent was removed by evaporation, yielding 7.54 g of dark red oil.

EXAMPLE XV

This example illustrates the preparation of N- -palmitoyl-N- -(N-4-nitrobenzo-2-oxa-1,3-diazole) lysine.

N- -(N-4-nitrobenzo-2-oxa-1,3-diazole) lysine (7.54 g) was dissolved in 150 ml of pyridine. Palmitoyl chloride (4.8 g) was added and the mixture stirred for 15 minutes. The solvent was removed by evaporation and the residue purified by column chromatography on silica gel using methylene chloride:methanol:acetic acid (100:5:2) as the solvent system. After removal of the solvent, 5.66 g of pure material was obtained.

What is claimed is:

1. A method of determing fetal lung maturity comprising measuring the ratio of surfactant to albumin in a sample of amniotic fluid from a test subject and comparing the measured ratio to a standard and thereby determining the maturation of the fetal lung.

2. The method of claim 1 wherein the ratio of surfactant to albumin is determined by measuring the fluorescence polarization of a fluorescent probe added to the amniotic fluid sample and comparing the measured fluorescence polarization to said standard said standard comprising a standardized curve generated from the measured fluorescence polarization of a set of calibrators adjusted to match the fluorescence polarization of solutions containing a known concentration of phospholipid and albumin.

3. The method of claim 1 wherein the ratio of surfactant to albumin is determined by measuring the fluorescence intensity of a fluorescent probe added to the amniotic fluid sample and comparing the measured fluorescence intensity to said standard said standard comprising a standardized curve generated from the measured fluorescence intensity of a set of calibrators adjusted to match the fluorescence intensity of solutions containing a known concentration of phospholipid and albumin.

\* \* \* \* \*